United States Patent
Hagiwara (10) Patent No.: US 11,754,528 B2
(45) Date of Patent: Sep. 12, 2023

(54) GAS DETECTION DEVICE

(71) Applicant: TAIYO YUDEN CO., LTD., Tokyo (JP)

(72) Inventor: Yasuhito Hagiwara, Tokyo (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 0 days.

(21) Appl. No.: 17/893,089

(22) Filed: Aug. 22, 2022

(65) Prior Publication Data

US 2022/0397555 A1 Dec. 15, 2022

Related U.S. Application Data (63) Continuation of application No. PCT/JP2021/007759, filed on Mar. 1, 2021.

(30) Foreign Application Priority Data

Feb. 28, 2020 (JP) .................................. 2020-032568

(51) Int. Cl.
*G01N 29/02* (2006.01)
*G01N 33/00* (2006.01)

(52) U.S. Cl.
CPC ....... *G01N 29/022* (2013.01); *G01N 33/0031* (2013.01); *G01N 2291/021* (2013.01)

(58) Field of Classification Search
CPC .............. G01N 29/022; G01N 33/0031; G01N 2291/021; G01N 2291/0255; G01N 2291/0256; G01N 2291/0426; G01N 5/02
See application file for complete search history.

(56) References Cited

U.S. PATENT DOCUMENTS

| | | | | |
|---|---|---|---|---|
| 10,295,457 | B1 * | 5/2019 | Ocheltree | G01N 33/0031 |
| 2002/0017467 | A1 * | 2/2002 | Ando | F02D 41/2474 |
| | | | | 204/426 |

(Continued)

FOREIGN PATENT DOCUMENTS

| | | | | |
|---|---|---|---|---|
| EP | 2589946 A2 * | 5/2013 | | G01M 3/16 |
| JP | H9-304244 A | 11/1997 | | |

(Continued)

OTHER PUBLICATIONS

Selyanchin, Roman, Wakamatsu, Shunichi, Hayashi, Kenshi, Lee, Seung-Woo, "A Nano-Thin Film-Based Prototype QCM Sensor Array for Monitoring Human Breath and Respiratory Patterns", Sensors, Jul. 31, 2015, vol. 15, No. 8, pp. 18834-18850, doi:10.3390/s150818834 entire text, all drawings.

(Continued)

*Primary Examiner* — Francis C Gray
(74) *Attorney, Agent, or Firm* — CHEN YOSHIMURA LLP

(57) ABSTRACT

A gas detection device according to an embodiment of the present invention includes a casing and a plurality of sensor elements. The casing includes a gas introducing port, a first chamber that communicates with the introducing port, a second chamber that communicates with the first chamber, a flow limiter that limits a flow of gas from the first chamber to the second chamber, and a gas exhausting portion that communicates with the second chamber. The plurality of sensor elements are disposed within the second chamber and have different detection sensitivities depending on a gas type.

10 Claims, 6 Drawing Sheets

(A)

(B)

(C)

(56) References Cited

U.S. PATENT DOCUMENTS

| | | | |
|---|---|---|---|
| 2016/0209436 A1 | 7/2016 | Wu et al. | |
| 2017/0363596 A1* | 12/2017 | Adachi | G01N 27/4077 |
| 2018/0266995 A1 | 9/2018 | Hattori et al. | |
| 2019/0063421 A1* | 2/2019 | Mou | G01N 33/0009 |
| 2019/0265180 A1 | 8/2019 | Inoue et al. | |
| 2019/0302072 A1* | 10/2019 | Mou | G01N 33/004 |
| 2021/0003543 A1* | 1/2021 | Hattori | G01N 33/0031 |

FOREIGN PATENT DOCUMENTS

| | | |
|---|---|---|
| JP | 3094415 U | 6/2003 |
| JP | 2015-206640 A | 11/2015 |
| JP | 2018-100868 A | 6/2018 |
| JP | 2018-155576 A | 10/2018 |
| JP | 2018-194314 A | 12/2018 |
| WO | 2019/121841 A1 | 6/2019 |

OTHER PUBLICATIONS

International Search Report (ISR) issued in PCT/JP2021/007759 dated May 2021.
Written Opinion (PCT/ISA/237) issued in PCT/JP2021/007759 dated May 2021. Concise Explanation of Relevance: This Written Opinion considers that the claims are not described by or obvious over the U.S. Patent Publication No. 2).

* cited by examiner

GAS DETECTION DEVICE

TECHNICAL FIELD

The present invention relates to a highly sensitive gas detection device.

BACKGROUND ART

In conventional highly sensitive gas detection devices, it is general that a plurality of sensor elements are arranged to identify a gas molecular species. In order to allow a target gas to flow in, it is also general to use fans, pumps, or the like to forcedly transport the gas to the sensor elements (see, e.g., Patent Literatures 1 and 2).

CITATION LIST

Patent Literature

Patent Literature 1: Japanese Patent Application Laid-open No. 2018-155576
Patent Literature 2: Japanese Utility Model Registration No. 3094415

DISCLOSURE OF INVENTION

Technical Problem

In transporting a detection gas to a plurality of sensor elements, the detection gas may be unevenly transported depending on the positions of the sensor elements, thus causing a detection error due to the positions of the sensor elements. Further, if a reference gas and a detection gas are selectively transported using pumps, it is necessary to arrange a plurality of pumps, but the gas transported to the sensor elements may be unevenly transported depending on the positions of the pumps.

If a plurality of sensor elements and pumps are arranged as described above, the arrangement thereof becomes complicated, which may deteriorate airtightness and may increase assembly man-hours.

In view of the circumstances as described above, it is an object of the present invention to provide a gas detection device capable of uniformly supplying gas to a plurality of sensor elements.

Solution to Problem

To achieve the above object, a gas detection device according to an embodiment of the present invention includes a casing and a plurality of sensor elements.

The casing includes a gas introducing port, a first chamber that communicates with the introducing port, a second chamber that communicates with the first chamber, a flow limiter that limits a flow of gas from the first chamber to the second chamber, and a gas exhausting portion that communicates with the second chamber. The plurality of sensor elements are disposed within the second chamber and have different detection sensitivities depending on a gas type.

The casing may include a wiring board including a first main surface on which the plurality of sensor elements are mounted, and a case main body attached to a peripheral portion of the first main surface in an airtight manner. The first chamber and the second chamber may be partitioned between the wiring board and the case main body.

The gas introducing port may be provided to the wiring board. The gas exhausting portion may be provided to the case main body.

The wiring board may further include a second main surface opposite to the first main surface. The gas introducing port may include a pump element mounted on the second main surface of the wiring board.

The case main body may include an open end fixed to the first main surface of the wiring board, a first bottom surface facing the first main surface of the wiring board and formed at a first height from the open end, and a second bottom surface facing the first main surface of the wiring board and formed at a second height lower than the first height from the open end.

In this case, a difference between the first height and the second height may be equal to or less than half of the first height.

The case main body may include a bottom portion facing the first main surface of the wiring board. The flow limiter may include a wall-like protrusion erected from the bottom portion of the case main body or from the first main surface of the wiring board.

The casing may include a first case main body and a second case main body coupled together to define the first chamber, the second chamber, and the flow limiter therein, the second case main body having the gas introducing port. The plurality of sensor elements may be disposed in the first case main body or the second case main body.

The first case main body may include an open end fixed to the second case main body, a first bottom surface formed at a first height from the open end, and a second bottom surface formed at a second height lower than the first height from the open end.

In this case, a difference between the first height and the second height may be equal to or less than half of the first height.

The gas exhausting portion may have a flow path cross-sectional area smaller than the second chamber.

Advantageous Effects of Invention

According to the present invention, it is possible to uniformly supply gas to a plurality of sensor elements and to improve measurement accuracy of a gas detection device.

MODES FOR CARRYING OUT THE INVENTION

Embodiments according to the present invention will be described below with reference to the drawings.

First Embodiment

[Configuration of Gas Detection Device]

Figure 1:
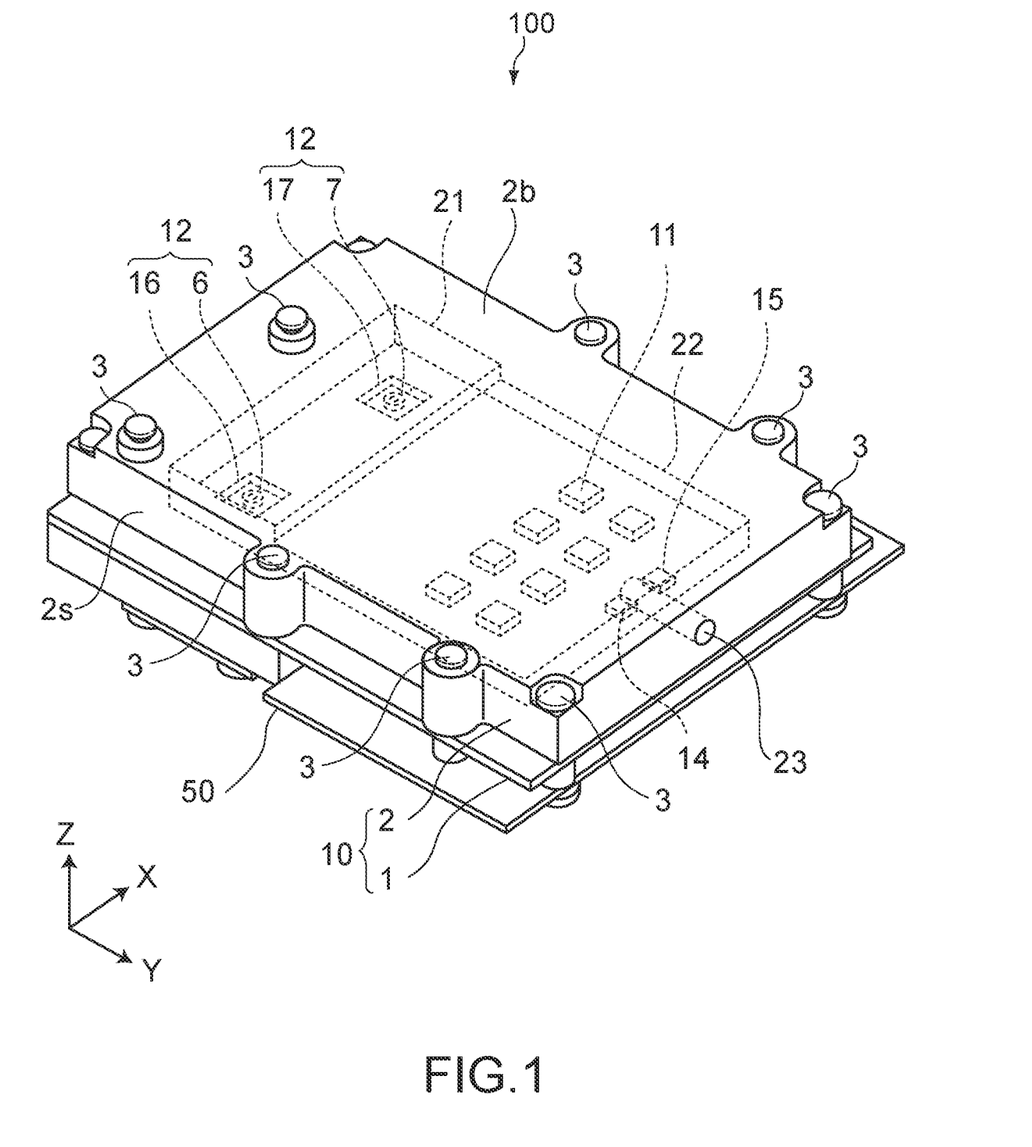
FIG. 1 is a perspective view of a gas detection device according to a first embodiment of the present invention.

FIG. 1 is a perspective view of a gas detection device 100 according to an embodiment of the present invention. In the drawing, the X-axis, the Y-axis, and the Z-axis represent three mutually orthogonal axial directions and correspond to the lateral (short side) direction, longitudinal (long side) direction, and height (thickness) direction of the gas detection device 100, respectively. The gas detection device 100 of this embodiment includes a casing 10 and a plurality of sensor elements 11 capable of detecting the type of gas introduced into the casing 10.

Figure 2:
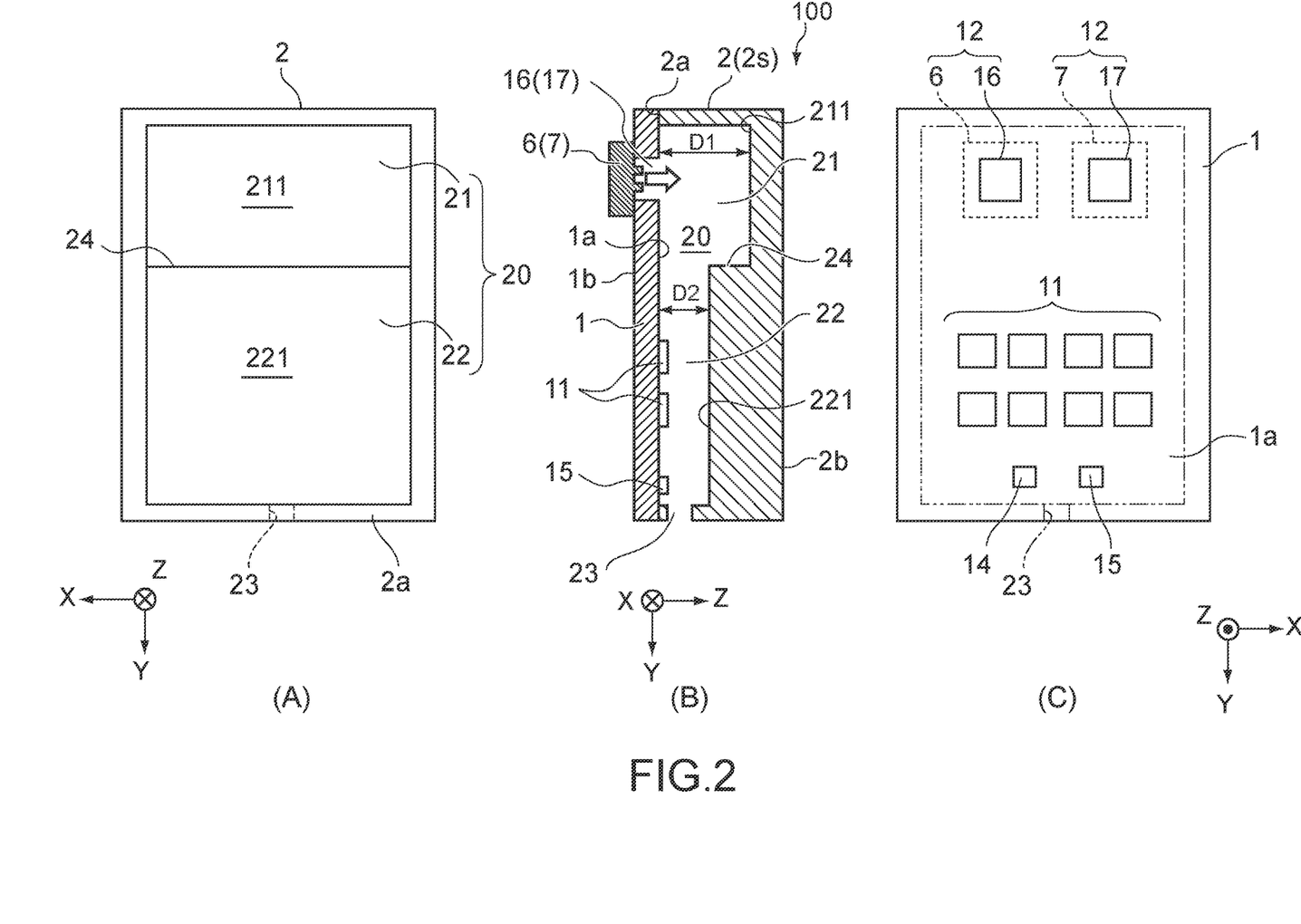
FIG. 2 shows the internal structure of the gas detection device, in which (A) is a plan view showing the inside of a case main body, (B) is a side cross-sectional view of the gas detection device, and (C) is a plan view of the inner side of a wiring board.

The casing 10 includes a wiring board 1 and a case main body 2 and is configured by combining them. FIG. 2 is a view showing the internal structure of the gas detection device 100, in which (A) is a plan view showing the inside of the case main body 2, (B) is a side cross-sectional view of the gas detection device 100, and (C) is a plan view of the inner side of the wiring board 1.

The wiring board 1 includes a first main surface 1a on which the plurality of sensor elements 11 are mounted, and a second main surface 1b on the opposite side. The first main surface 1a is an inner main surface facing the case main body 2, and the second main surface 1b is an outer main surface exposed to the outside.

The wiring board 1 is a rectangular substrate having the long side in the Y-axis direction and is typically a double-sided wiring board including wiring layers formed on the first main surface 1a and the second main surface 1b. The wiring board 1 is typically a glass epoxy substrate, but in addition thereto, another substrate having rigidity, such as a ceramic substrate or a metal substrate, can be employed.

The case main body 2 has the shape of a substantially rectangular parallelepiped, from which one surface parallel to the X-Y plane is removed to form an opening. The case main body 2 includes a peripheral wall portion 2s and a bottom portion 2b that partition a gas introducing space 20. The peripheral wall portion 2s includes an open end 2a that is an end forming the opening of the case main body 2. The open end 2a is fixed at the peripheral portion of the first main surface 1a of the wiring board 1 so as to maintain airtightness. The bottom portion 2b is located at a position facing the first main surface 1a of the wiring board 1. Thus, the gas introducing space 20 is formed between the wiring board 1 and the case main body 2.

In this embodiment, the case main body 2 is fixed to the wiring board 1 by a plurality of screw members. A sealing member (packing etc.) (not shown) is disposed between the first main surface 1a of the wiring board 1 and the open end 2a of the case main body 2, so that the airtightness between the wiring board 1 and the case main body 2 is ensured. The case main body 2 is, for example, an injection molded body of a synthetic resin material. The type of the resin material is not particularly limited and is, for example, polytetrafluoroethylene.

The casing 10 includes gas introducing portions 12, the gas introducing space 20, and a gas exhausting portion 23. The gas introducing portions 12 are provided in the wiring board 1, and the gas introducing space 20 and the gas exhausting portion 23 are provided in the case main body 2.

The gas introducing portions 12 include a pair of gas introducing ports (or simply referred to as "introducing ports") 16 and 17 drilled in the wiring board 1, and pump elements 6 and 7 disposed at the respective introducing ports. The introducing ports 16 and 17 are hole portions penetrating the wiring board 1 in the thickness direction thereof. The shape of the introducing ports 16 and 17 is not limited to be rectangular as shown in the figure, and it may be circular. The pump elements 6 and 7 are connected to a gas source (not shown) and sends gas from the gas source to the gas introducing space 20. The type of the pump elements 6 and 7 is not particularly limited. In this embodiment, the pump elements 6 and 7 are, for example, motor-type or piezo-type micro-diaphragm pumps mounted on the second main surface 1b of the wiring board 1.

The plurality (two) of gas introducing portions 12 are provided in this embodiment, but a single or three or more gas introducing portions 12 may be provided. One of the gas introducing portions 12 (6, 16) is a gas introducing portion for a reference gas, and the other gas introducing portion 12 (7, 17) is a gas introducing portion for a detection target gas. The reference gas is typically dry air. The detection target gas is appropriately selected according to specifications and applications. For example, $CO_2$, $C_6H_6$, $CO$, $NH_3$, and $O_2$ may be used for the detection target gas.

The position where each gas introducing portion 12 is formed is not particularly limited, but in this embodiment, as shown in (C) of FIG. 2, the gas introducing portions 12 are provided in a region on one side (the −Y direction side) of the wiring board 1 in the longitudinal direction so as to be adjacent to each other in the lateral direction. Not that the gas introducing portions 12 are not limited to the example in which they are provided on the wiring board 1, and they may be provided on the case main body 2.

The gas introducing space 20 is divided into a first chamber 21 and a second chamber 22. The first chamber 21 is provided at a position immediately below the gas introducing portions 12 so as to communicate with the introducing ports 16 and 17 of the gas introducing portions 12. The second chamber 22 is provided between the first chamber 21 and the gas exhausting portion 23 so as to communicate with the first chamber 22.

The case main body 2 includes a first bottom surface 211 facing the first main surface 1a of the wiring board 1 and formed at a first height D1 from the open end 2a, and a second bottom surface 221 facing the first main surface 1a of the wiring board 1 and formed at a second height D2 shallower than the first height D1 from the open end 2a. The first chamber 21 is a space between the first main surface 1a and the first bottom surface 211, and the second chamber 22 is a space between the first main surface 1a and the second bottom surface 221. A step portion 24 is formed between the first bottom surface 211 and the second bottom surface 221. The step portion 24 is formed at the boundary between the first chamber 21 and the second chamber 22.

The step portion 24 is provided so as to extend in the lateral direction (X-axis direction) between the gas introducing portion 12 and the gas exhausting portion 23 as viewed from the wiring board 1. The step portion 24 is a wall surface extending in the perpendicular direction toward the wiring board 1 from the bottom portion 2b of the case main body 2 and forms a flow limiter for limiting the flow path of the gas flowing from the first chamber 21 towards the second chamber 22. The height of the step portion 24, which is the difference between the first height D1 and the second height D2 (D1-D2), is not particularly limited, but it is formed at an appropriate height capable of limiting the inflow of the gas, which has been introduced into the first chamber 21, into the second chamber 22. In this embodiment, the height of the step portion 24 is set to have a size equal to or less than half of the height of the first chamber 21.

The gas exhausting portion 23 is a through-hole formed in the side wall on the other side (+Y direction side) in the longitudinal direction of the case main body 2 so as to communicate with the second chamber 22. The gas exhausting portion 23 has a smaller flow path cross-sectional area than the second chamber 22. The flow path cross-sectional area is the area of the flow path perpendicular to the gas flow direction. The shape of the gas exhausting portion 23 is not particularly limited and may be rectangular, circular, elliptical, or the like. Further, the gas exhausting portion 23 may be a set of a plurality of through-holes.

The plurality of sensor elements 11 have respective detection sensitivities that differ depending on the gas type, and are quartz crystal microbalances (QCMs), for example. The QCM is a mass sensor that measures a minute amount of mass change by utilizing the property that a resonance frequency fluctuates (drops) in accordance with the mass of a substance to be detected (gas) when the substance adheres to the electrode surface of the quartz oscillator. Note that the sensor element 11 is not limited to the example of the QCM sensor and may be a semiconductor sensor capable of detecting a specific gas type.

The plurality of sensor elements 11 are mounted on the first main surface 1a of the wiring board 1 facing the gas introducing space 20. Each sensor element 11 includes a sensitive membrane for adsorbing the detection target gas on the electrode surface of the quartz oscillator. The sensitive membrane is made of a different material for each sensor element 11. In this embodiment, the eight sensor elements 11 are provided, and different sensitive membranes are used for the respective sensor elements 11, so that eight kinds of gases can be detected.

Note that the present invention is not limited to the example in which one type of gas is detected by one sensor element 11, and one type of gas may be detected by a plurality of sensor elements 11. In addition, a plurality of kinds of gases may be detected by one sensor element 11. In this case, it is favorable to use a sensitive membrane having a different sensitivity depending on the type of gas.

The plurality of sensor elements 11 are disposed on the first main surface 1a of the wiring board 1 in the region facing the second chamber 22. In this embodiment, the example in which the eight sensor elements 11 are arranged in two rows by four columns is shown, but the layout is not limited to this. Further, the number of sensor elements 11 is not limited to eight and can be optionally set in accordance with the number of gas types to be detected.

A temperature sensor 14 and a humidity sensor 15 are mounted on the first main surface 1a of the wiring board 1. The mounting region for the temperature sensor 14 and the humidity sensor 15 is not particularly limited. In this embodiment, the temperature sensor 14 and the humidity sensor 15 are disposed in any region between the sensor element 11 and the gas exhausting portion 23. If the sensor element 11 has the QCM characteristic of a temperature dependence, the output of the sensor element 11 is corrected on the basis of the output of the temperature sensor 14. Further, the humidity sensor 15 may be used as a detection sensor for water vapor, for example. For example, a thermistor is applicable to the temperature sensor 14, and a QCM sensor including a sensitive membrane having adsorption property with respect to water vapor is applicable to the humidity sensor 15. Note that at least one of the temperature sensor 14 and the humidity sensor 15 may be omitted if necessary.

As shown in FIG. 1, a control board 50 is installed on the second main surface 1b of the wiring board 1. A power supply circuit and a signal processing circuit are connected to the control board 50. The control board 50 is electrically connected to the wiring board 1 to supply the necessary power to each sensor element 11, the pump elements 6 and 7, the temperature sensor 14, and the humidity sensor 15 via the wiring layers on the wiring board 1. The signal processing circuit detects the presence or absence, the type, the amount, and the like of the detection target gas in the gas introducing space 20 on the basis of the outputs of the sensor elements 11, the temperature sensor 14, and the humidity sensor 15. Note that the control board 50 may mount, in addition to the elements or sensors described above, other electronic components (e.g., a drive circuit of the pump elements 6 and 7 and the like).

[Operation of Gas Detection Device]

Next, a typical operation of the gas detection device 100 of this embodiment configured as described above will be described.

First, the pump element 6 for introducing a reference gas is driven to introduce the reference gas into the gas introducing space 20, and the output of each sensor element 11 is calibrated. Subsequently, the driving of the pump element 6 is stopped, and the pump element 7 for introducing a detection target gas is driven to introduce the detection target gas to the gas introducing space 20. The detection target gas to be introduced is typically a gas detected by any sensor element 11 of the plurality of sensor elements 11, but of course it may be other gases. Hereinafter, the detection target gas will be simply referred to as gas.

The gas introduced from the gas introducing portion 12 (7, 17) passes through the first chamber 21, the second chamber 22, and the gas exhausting portion 23 in the stated order in the gas detection device 100. (A) to (C) of FIG. 3 are schematic views showing the flow of gas in the respective portions shown in (A) to (C) of FIG. 2 by white arrows.

Figure 3:
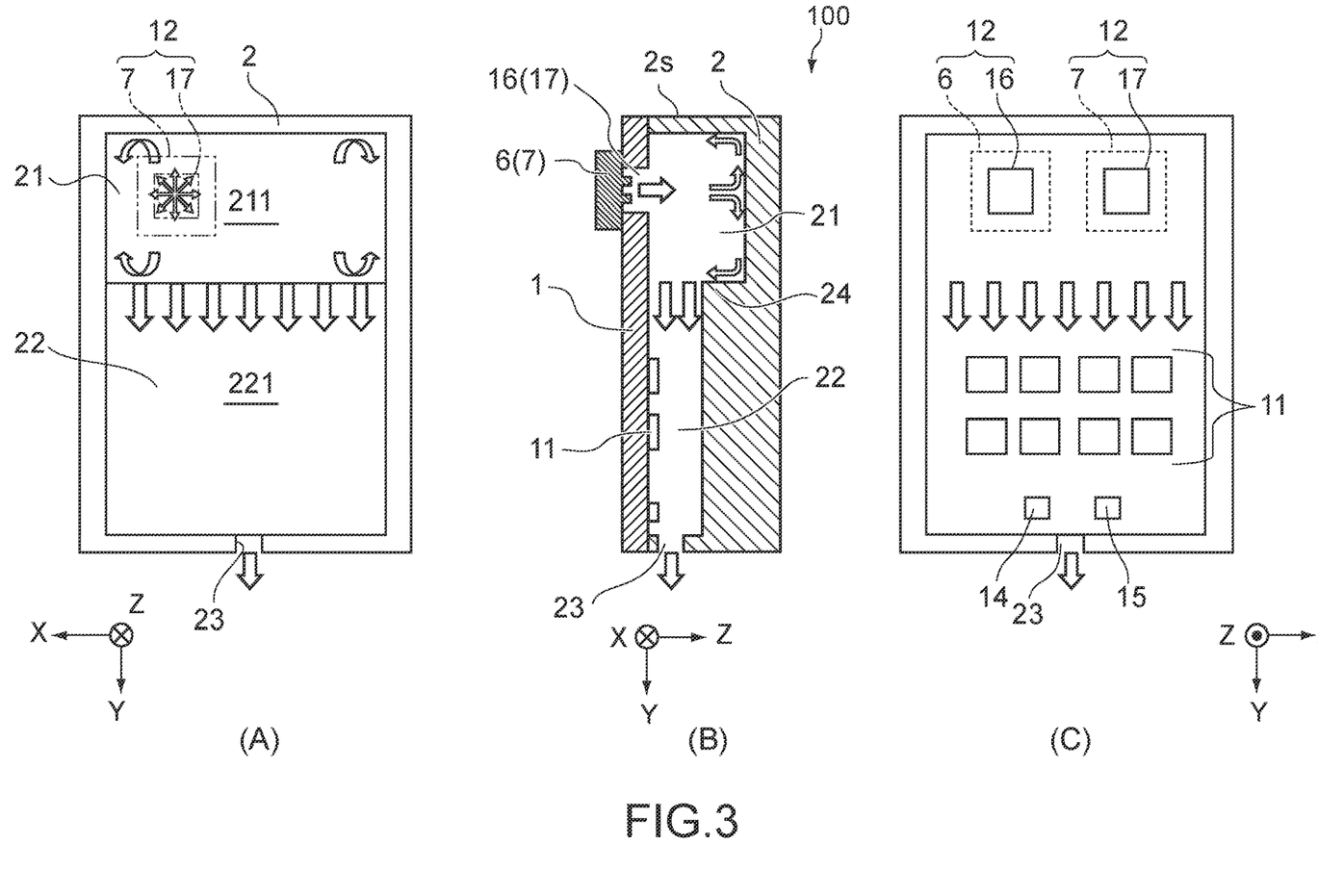
FIG. 3 shows the flow of gas in each of the portions (A) to (C) of FIG. 2, respectively, by white arrows.

As shown in (A) and (B) of FIG. 3, the gas introduced from the gas introducing portion 12 to the first chamber 21 is restrained from flowing in the second chamber 22 by the step portion 24, and is thus isotropically diffused in the first chamber 21 in a turbulent state. In other words, the step portion 24 acts as a flow limiter creating a narrow passage from the first chamber 21 towards the second chamber 22 (although the second chamber 22 has the same cross section as the passage in this case), and causes the gas introduced into the first chamber 21 to flow into the second chamber 22 in a laminar flow state.

Hence, it is possible to uniformly supply the gas introduced into the first chamber 21 over the entire region of the second chamber 22 regardless of the position of the gas introducing portion 12. Further, since the gas introducing portion 12 is provided to the wiring board 1 so as to face the bottom of the first chamber 21 (first bottom surface 211), it is possible to further enhance the diffusion effect of the gas in the first chamber 21.

On the other hand, the gas flowing into the second chamber 22 flows toward the gas exhausting portion 23 along the first main surface 1a of the wiring board 1 on which the plurality of sensor elements 11 are mounted. Since the gas exhausting portion 23 has a smaller flow path cross-sectional area than the second chamber 22, the pressure of the gas in the second chamber 22 is higher than the pressure on the outlet side of the gas exhausting portion 23. This makes it possible to improve the detection sensitivity of the gas in the sensor element 11. Further, since the gas flowing into the second chamber 22 flows toward the gas exhausting portion 23 in a laminar flow state, the gas is uniformly supplied to the plurality of sensor elements 11 on the wiring board 1. This can achieve highly accurate gas detection operation regardless of the position of the sensor element 11.

Figure 4:
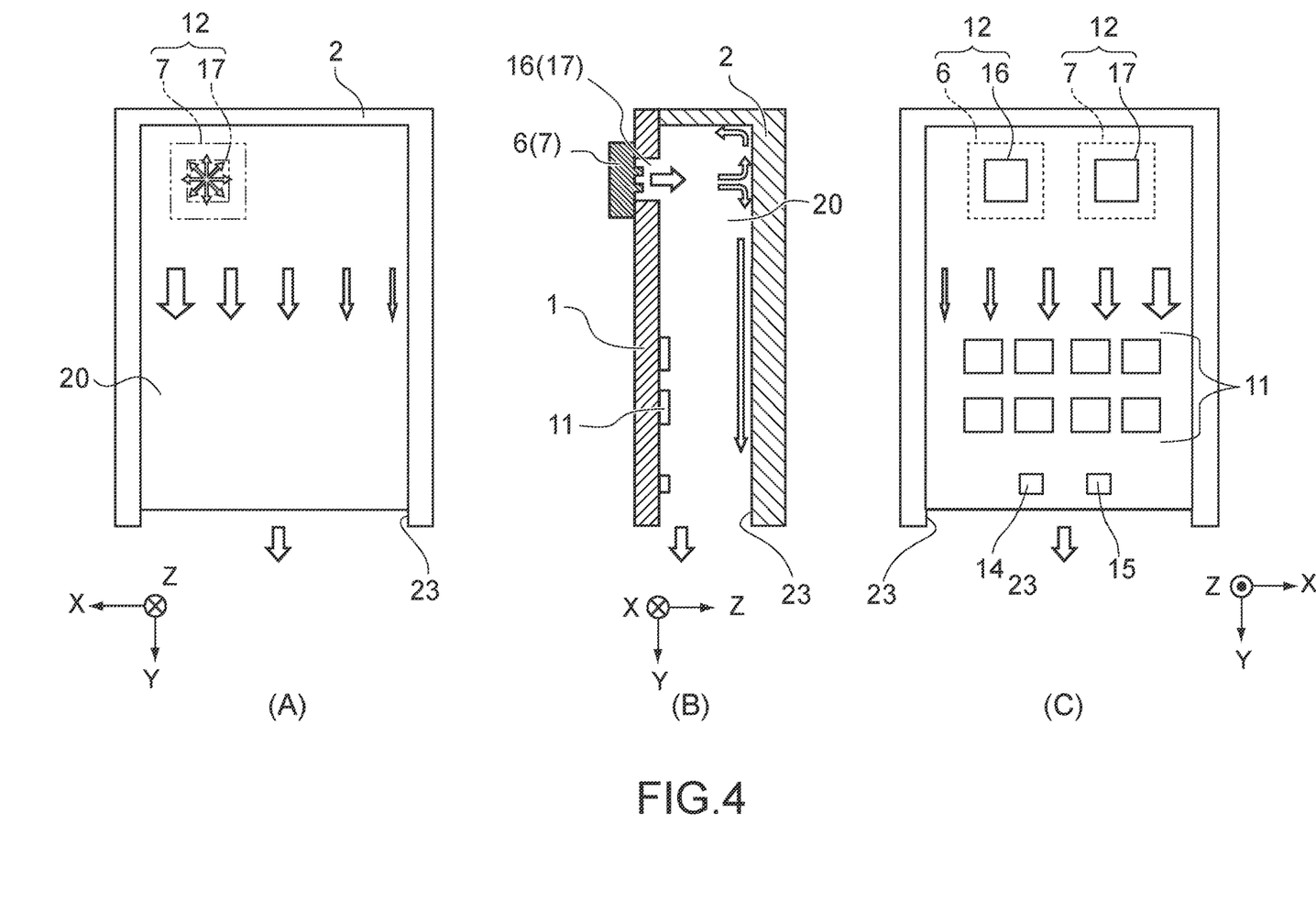
FIG. 4 is similar to FIG. 3, showing the gas flow in a gas detection device according to a comparative example.

For example, as a comparative example, (A) to (C) of FIG. 4 schematically show the flow of gas when the gas introducing space 20 does not include the step portion 24 and when the gas exhausting portion 23 is formed to have the same width and height as those of the gas introducing space. In this case, since the gas introducing space 20 does not include the step portion 24 (see FIG. 3) forming a narrow passage, the flow rate of the gas in the gas introducing space 20 tends to increase in the region closer to the gas introducing portion 12 (7, 17) and decrease in the region farther from the gas introducing portion 12 (7, 17). Therefore, since the gas does not uniformly contact the sensor elements 11, the detection sensitivity may vary depending on the position of the sensor element 11, and the detection accuracy of the gas may deteriorate.

On the other hand, according to this embodiment, as described above, since the gas can be uniformly transported to the plurality of sensor elements 11 having different detection sensitivities depending on the gas type, it is possible to perform highly accurate gas detection operation regardless of the gas introduction position or the position of the sensor element. As a result, the identification of the introduced gas, the amount thereof, and the like can be detected with high accuracy.

Further, it is also possible to identify the type of the introduced gas on the basis of the outputs of the plurality of sensor elements 11 even when the type of the introduced gas is unknown. Conventionally, a sensor element prepared for a specific gas to be a target has been necessary, and it is impossible to identify the gas type of an unknown gas. However, according to this embodiment, it is possible to uniformly supply gas to a plurality of sensors, and thus possible to perform the identification of the gas type and the measurement of gas concentration at the same time.

Further, although a plurality of pumps have been necessary to be disposed for the case of calibrating the sensors using the reference gas or for each sensor element, the gas type detection can be performed by providing one pump to each of the reference gas and the detection gas and by providing one pump to the plurality of sensors for the detection gas. This makes it possible to dispose the pumps and the sensors on the same substrate, so that a large merit can be obtained in terms of the manufacturing cost, the miniaturization and weight reduction, and the like.

Second Embodiment

Figure 5:
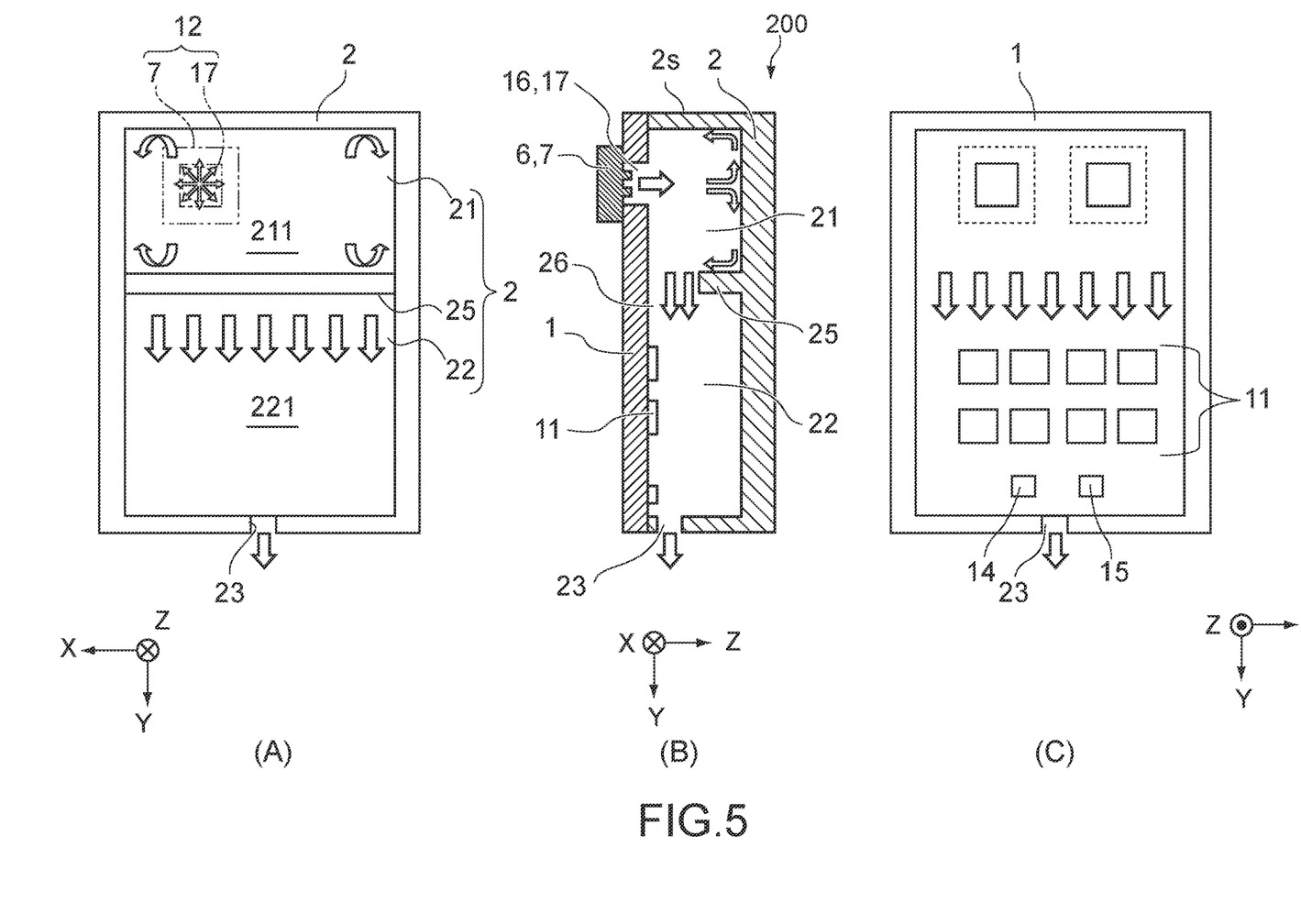
FIG. 5 shows the internal structure of a gas detection device according to a second embodiment of the present invention, in which (A) is a plan view showing the inside of a case main body, (B) is a side cross-sectional view of the gas detection device, and (C) is a plan view of the inner side of a wiring board.

FIG. 5 shows a configuration of a gas detection device 200 according to a second embodiment of the present invention, in which (A) is a plan view showing the inside of a case main body 2, (B) is a side cross-sectional view of the gas detection device 200, and (C) is a plan view of the inner side of a wiring board 1.

Hereinafter, the constituent elements different from those of the first embodiment will be mainly described, and the constituent elements similar to those of the first embodiment will be denoted by similar reference symbols, and description thereof will be omitted or simplified.

The gas detection device 200 of this embodiment is different from that of the first embodiment in that both first and second chambers 21 and 22 constituting a gas introducing space 20 are formed at the same depth, and a wall-like protrusion 25 is provided between the first and second chambers 21 and 22 as a flow limiter that limits the flow of the gas.

As shown in (A) and (B) of FIG. 5, the wall-like protrusion 25 is erected on a bottom portion 2b of the case main body 2 so as to linearly extend in the lateral direction (X-axis direction), and forms a boundary between the first chamber 21 and the second chamber 22. The height of the wall-like protrusion 25 is not particularly limited, but it is formed to have an appropriate height capable of limiting the inflow of the gas, which has been introduced into the first chamber 21, into the second chamber 22. In this embodiment, the height of the wall-like protrusion 25 is set to have a size be equal to or less than half of the height of the first chamber 21. The width of the wall-like protrusion 25 (width dimension along the Y-axis direction) is not particularly limited.

Also in the gas detection device 200 of this embodiment configured as described above, the action effect similar to that of the first embodiment can be obtained. According to this embodiment, the above-mentioned action effect can be obtained only by forming the wall-like protrusion 25 on the inner surface of the bottom portion 2b of the case main body 2, so that it is possible to reduce the volume of the materials constituting the case main body 2.

Note that this embodiment has described an example in which the wall-like protrusion 25 is erected on the bottom portion 2b of the case main body 2, but the present invention is not limited thereto. For example, the wall-like protrusion 25 may be erected on a first main surface 1a of the wiring board 1, and the same effect as described above can be obtained in this case as well.

Third Embodiment

Figure 6:
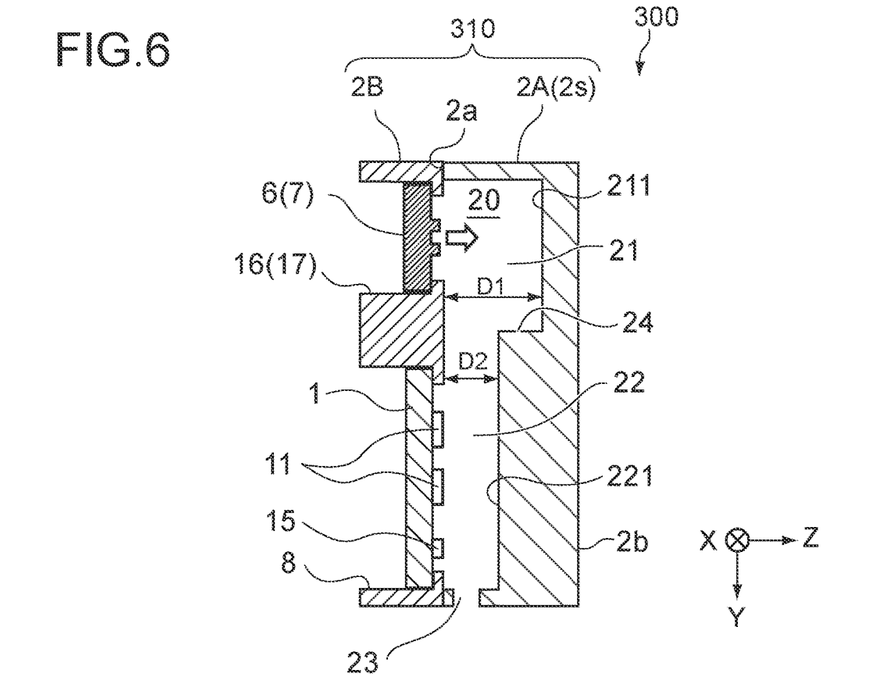
FIG. 6 is a side cross-sectional view showing the internal structure of a gas detection device according to a third embodiment of the present invention.

FIG. 6 is a side cross-sectional view showing a configuration of a gas detection device 300 according to a third embodiment of the present invention. Hereinafter, the constituent elements different from those of the first embodiment will be mainly described, and the constituent elements similar to those of the first embodiment will be denoted by similar reference symbols, and description thereof will be omitted or simplified.

The gas detection device 300 of this embodiment is different from that of the first embodiment described above in the structure of a casing 310 forming a gas introducing space 20. In this embodiment, a first case main body 2A and a second case main body 2B are combined.

The first case main body 2A corresponds to the case main body 2 in the first embodiment and includes a peripheral wall portion 2s and a bottom portion 2b that partition the gas introducing space 20, and a gas exhausting portion 23. An open end 2a, which is an end of the peripheral wall portion 2s, is airtightly fixed to the second case main body 2B. As in the first embodiment, the bottom portion 2b includes a first bottom surface 211 formed at a first height D1 from the open end 2a and a second bottom surface 221 formed at a second height D2 from the open end 2a.

The gas introducing space 20 is divided into a first chamber 21 and a second chamber 22. The first chamber 21 is a gap portion between the second case main body 2B and the first bottom surface 211, and the second chamber 22 is a gap portion between the second case main body 2B and the second bottom surface 221. A step portion 24 that forms the boundary between the first chamber 21 and the second chamber 22 is provided between the first bottom surface 211 and the second bottom surface 221. The height of the step portion 24, which is the difference between the first height D1 and the second height D2 (D1-D2), is set to have a size equal to or less than half of the height of the first chamber 21, for example.

The second case main body 2B is attached to the open end 2a of the first case main body 2A, and closes the gas introducing space 20. The second case main body 2B is formed of the material similar to that of the first case main body 2A. In this embodiment, the second case main body 2B is formed of a molded body of a synthetic resin material.

The second case main body 2B includes a housing portion 8 for housing a wiring board 1 on which a plurality of sensor elements 11 are mounted. The housing portion 8 is a through-hole formed in the second case main body 2B in the thickness direction thereof (Z-axis direction), and the wiring board 1 is airtightly fixed to the housing portion 8 such that the plurality of sensor elements 11 face the second bottom surface 221. As a result, the plurality of sensor elements 11 are disposed in the second chamber 22.

The second case main body 2B includes a pair of introducing ports 16 and 17 for housing pump elements 6 and 7. The pair of introducing ports 16 and 17 are through-holes formed in the second case main body 2B in the thickness direction thereof (Z-axis direction), and the pump elements 6 and 7 are airtightly fixed to the pair of introducing ports 16 and 17 so as to face the first bottom surface 211. This embodiment is different from the first embodiment in that the pump elements 6 and 7 are directly disposed not on the wiring board 1 but in the introducing ports 16 and 17. Further, the pump elements 6 and 7 are electrically connected to a drive circuit mounted on the control board 50 (see FIG. 1), for example.

Also in the gas detection device 300 of this embodiment configured as described above, the action effect similar to those of the embodiments described above can be obtained. In this embodiment, since the casing 310 is configured by the first case main body 2A and the second case main body 2B, it is possible to improve the strength of the casing 310 and to miniaturize the wiring board 1 on which the plurality of sensor elements 11 are mounted.

Fourth Embodiment

Figure 7:
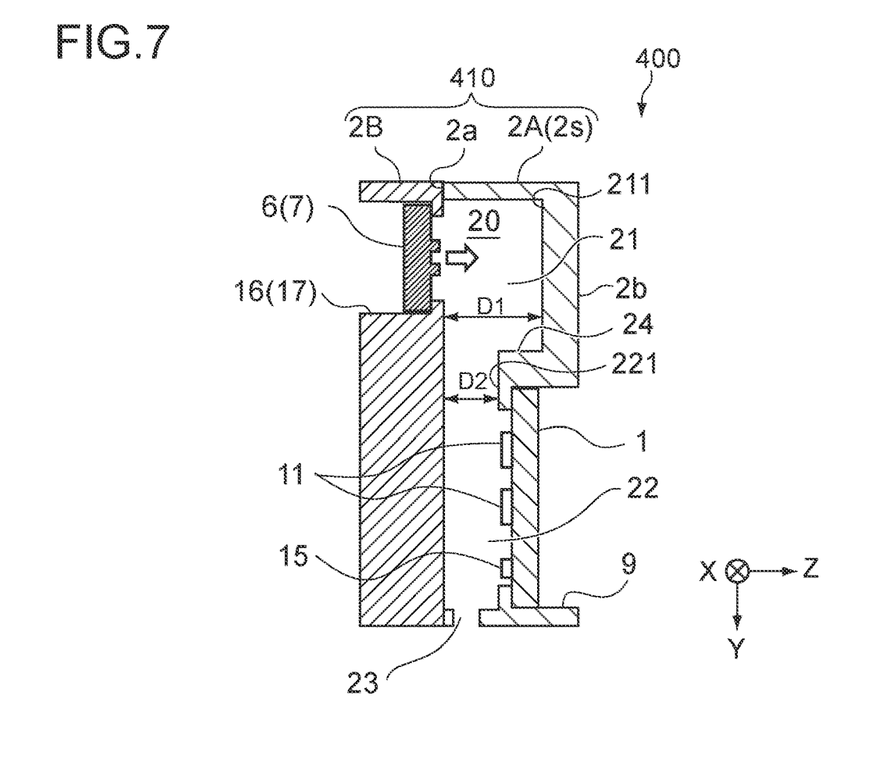
FIG. 7 is a side cross-sectional view showing the internal structure of a gas detection device according to a fourth embodiment of the present invention.

FIG. 7 is a side cross-sectional view showing a configuration of a gas detection device 400 according to a fourth embodiment of the present invention. Hereinafter, the constituent elements different from those of the third embodiment will be mainly described, and the constituent elements similar to those of the third embodiment will be denoted by similar reference symbols, and description thereof will be omitted or simplified.

The gas detection device 400 of this embodiment is different from that of the third embodiment described above in that a wiring board 1 for mounting a plurality of sensor elements 11 is disposed in a first case main body 2A.

In this embodiment, the first case main body 2A includes a housing portion 9 for housing the wiring board 1 on which the plurality of sensor elements 11 are mounted. The housing portion 9 is a through-hole formed in the first case main body 2A in the thickness direction thereof (Z-axis direction), and the wiring board 1 is airtightly fixed to the housing portion 9 such that the plurality of sensor elements 11 are disposed in a second chamber 22.

Also in the gas detection device 400 of this embodiment configured as described above, the action effect similar to those of the embodiments described above can be obtained. Note that the pump elements 6 and 7 are disposed in the second case main body 2B, but the present invention is not limited thereto. The pump elements 6 and 7 may be disposed in the first case main body 2A similarly to the wiring board 1.

It will be apparent to those skilled in the art that various modifications and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

The invention claimed is:

1. A gas detection device, comprising:
    a casing including:
        a gas introducing port,
        a first chamber that communicates with the gas introducing port,
        a second chamber that communicates with the first chamber,
        a flow limiter that limits a flow of gas from the first chamber to the second chamber, and
        a gas exhausting portion that communicates with the second chamber; and
    a plurality of sensor elements disposed within the second chamber and having different detection sensitivities depending on a gas type.

2. The gas detection device according to claim 1, wherein the casing includes:
    a wiring board including a first main surface on which the plurality of sensor elements are mounted, and
    a case main body attached to a peripheral portion of the first main surface in an airtight manner, and
    wherein the first chamber and the second chamber are partitioned between the wiring board and the case main body.

3. The gas detection device according to claim 2, wherein:
    the gas introducing port is provided to the wiring board, and
    the gas exhausting portion is provided to the case main body.

4. The gas detection device according to claim 3, wherein:
    the wiring board further includes a second main surface opposite to the first main surface, and
    the gas introducing port includes a pump element mounted on the second main surface of the wiring board.

5. The gas detection device according to claim 2, wherein the case main body includes:
    an open end fixed to the first main surface of the wiring board,
    a first bottom surface facing the first main surface of the wiring board and formed at a first height from the open end, and
    a second bottom surface facing the first main surface of the wiring board and formed at a second height lower than the first height from the open end.

6. The gas detection device according to claim 2, wherein:
the case main body includes a bottom portion facing the first main surface of the wiring board, and
the flow limiter includes a wall-like protrusion erected from the bottom portion of the case main body or from the first main surface of the wiring board.

7. The gas detection device according to claim 1,
wherein the casing includes a first case main body and a second case main body coupled together to define the first chamber, the second chamber, and the flow limiter therein, the second case main body having the gas introducing port, and
wherein the plurality of sensor elements are disposed in the first case main body or the second case main body.

8. The gas detection device according to claim 7, wherein the first case main body includes:
an open end fixed to the second case main body,
a first bottom surface formed at a first height from the open end, and
a second bottom surface formed at a second height lower than the first height from the open end.

9. The gas detection device according to claim 5, wherein a difference between the first height and the second height is equal to or less than half of the first height.

10. The gas detection device according to claim 1, wherein the gas exhausting portion has a flow path cross-sectional area smaller than the second chamber.

* * * * *